United States Patent

Savornin

[11] Patent Number: 5,788,698
[45] Date of Patent: Aug. 4, 1998

[54] OSTEOSYNTHESIS CLIP AND ANCILLARY MATERIAL FOR ITS EMPLACEMENT

[76] Inventor: Claude Savornin, 69 Avenue de Paris, F-94160 Saint-Mande, France

[21] Appl. No.: 532,650

[22] PCT Filed: Apr. 18, 1994

[86] PCT No.: PCT/FR94/00433

§ 371 Date: Oct. 16, 1995

§ 102(e) Date: Oct. 16, 1995

[87] PCT Pub. No.: WO94/23654

PCT Pub. Date: Oct. 27, 1994

[30] Foreign Application Priority Data

Apr. 19, 1993 [FR] France .................. 93 04635

[51] Int. Cl.$^6$ .................. A61B 17/68
[52] U.S. Cl. .................. 606/75; 606/142
[58] Field of Search .................. 606/75, 72, 73, 606/60, 69, 70, 71, 219, 220, 216, 96, 99, 100, 104, 86, 142, 143

[56] References Cited

U.S. PATENT DOCUMENTS

| 2,789,558 | 4/1957 | Rush | 606/99 |
| 4,263,903 | 4/1981 | Griggs | 606/75 |
| 4,454,875 | 6/1984 | Pratt et al. | 606/75 |
| 4,848,328 | 7/1989 | Laboureau et al. | |
| 4,874,122 | 10/1989 | Froelich et al. | 606/219 |
| 5,053,038 | 10/1991 | Sheehan | |
| 5,395,372 | 3/1995 | Holt et al. | 606/61 |
| 5,454,814 | 10/1995 | Comte | 606/75 |

FOREIGN PATENT DOCUMENTS

| 301898 | 2/1989 | European Pat. Off. |
| 2 562 416 | 10/1985 | France |
| 597 838 | 4/1978 | Switzerland |
| 1 463 268 | 3/1989 | U.S.S.R. |
| 9200773 | 1/1992 | WIPO |
| WO92/17122 | 10/1992 | WIPO |

*Primary Examiner*—Guy V. Tucker
*Attorney, Agent, or Firm*—Young & Thompson

[57] ABSTRACT

An osteosynthesis clip consisting of a central member and two side members. The central member includes two portions with an outwardly-open obtuse angle therebetween, and the distal ends of the side members include a sloping portion defined by an inward-facing surface. Ancillary equipment for fitting the clip is also disclosed. The clip is characterized in that the side members converge at an angle of less than 20° and their outer surfaces have jagged portions which prevent withdrawal.

10 Claims, 3 Drawing Sheets

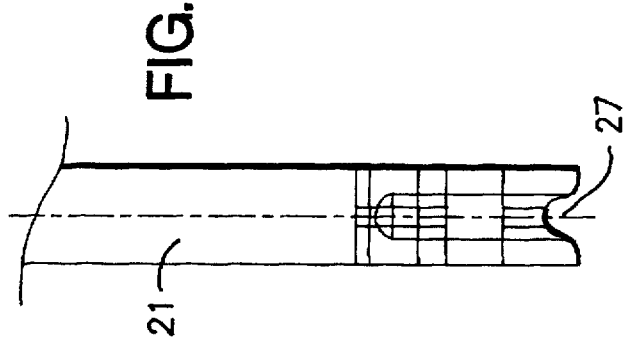
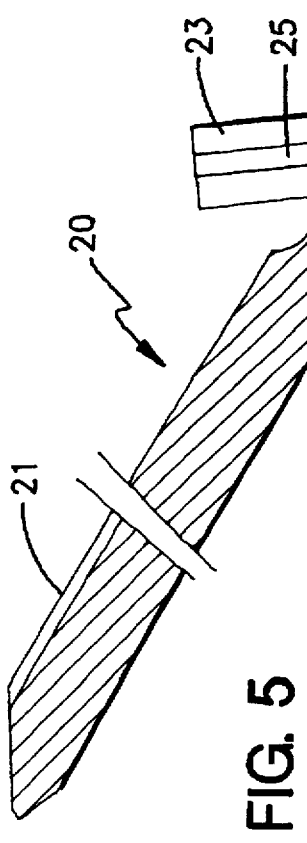
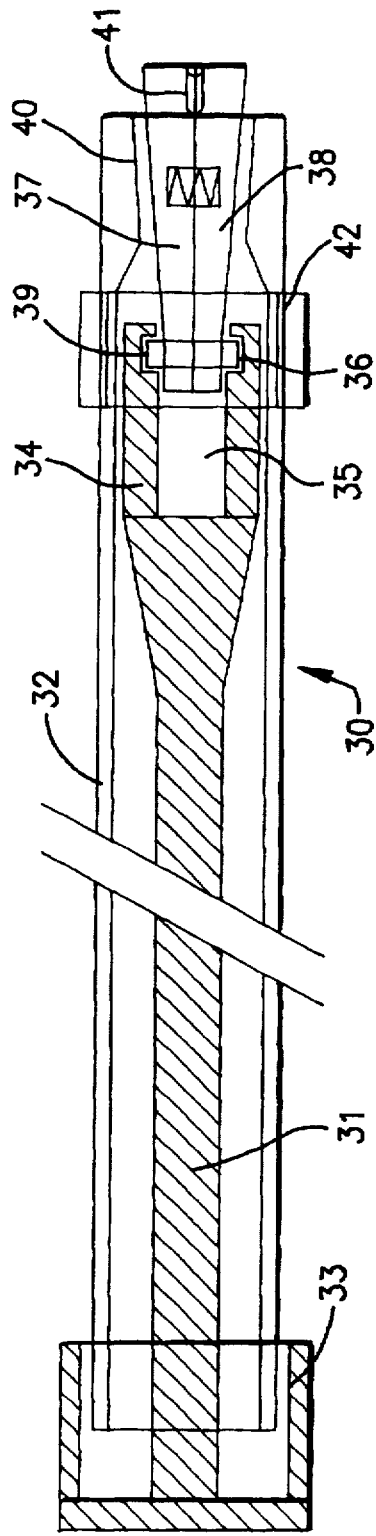

5,788,698

1

OSTEOSYNTHESIS CLIP AND ANCILLARY MATERIAL FOR ITS EMPLACEMENT

This application is filed under 35 USC 371 based on PCT/FR94/00433 which was filed on Apr. 18, 1994.

FIELD OF THE INVENTION

The present invention relates to an osteosynthesis clip adapted to secure the site of a fracture or osteotomy for its consolidation, as well as an ancillary material for emplacement of such a clip.

BACKGROUND OF THE INVENTION

Different osteosynthesis clips are known. There could be cited for example the clip described in FR-A-2.668.361, which is formed of a martensitic thermo-elastic alloy with shape memory. It comprises two legs, adapted to be inserted forcibly on opposite sides of the site of the fracture of the bone to be repaired, and a connecting base. The legs are trained to come together under the influence of temperature above the austenitic transformation temperature and the connecting base is trained to pass from rectilinear shape at a temperature lower than the martensitic transformation temperature, to a wavy shape giving rise to a shortening of its length, at a temperature higher than the austenitic transformation temperature. Such a clip has dynamic and auto-retention characteristics. However it does not permit adjusting precisely the position of the two bone fragments to be stabilized because the operator is not master of the shape transformation of this clip and cannot make tests with the clip before its use, which is to say before it has its final shape.

There is also known, from FR-A-2.562.416 (U.S. Pat. No. 4.848.328), an osteosynthesis clip constituted by a core to which are connected two lateral legs. The core comprises two parts inclined toward each other at an outwardly opening obtuse angle. The legs are divergent. The legs and the core have a square or rectangular cross section. Each of the legs comprises, on its internal surface, a succession of projections or saw teeth forming an anti-return device. Wings are provided on the frontal surfaces of each leg of the clip. Each of the legs terminates at its distal end in a bevel delimited by the outwardly opening surfaces in FR-A-2.562.416 and inwardly opening in U.S. Pat. No. 4.848.328. This clip is adapted essentially to secure the site of an osteotomy pending the consolidation of the latter, below the tibial plate. Such a clip, whose legs diverge, however does not permit good compression of the osteotomy site. On the contrary, it preferentially produces a distension, which is to say a spacing of the two bone fragments to be stabilized, because the memory of the metal tends to create a spacing.

For carpal scaphoidal fractures, there are known so-called Kirschner clips, which give mediocre stability and which are the object of frequent migration, the source of cutaneous irritation and tolerance problems. There are also known screws, which are difficult to emplace and which can give rise to a poor grip along a scaphoidal proximal pole of poor quality, particularly of the Schernberg II type. There are also known Herbert screws, but they have, in addition to the drawbacks recited above, the major defect of passing through a fundamental articulation of the first column which is the trapezial scapho articulation. As to clips of the Warner type available on the market, they are insufficient to bridge a loss of material from pseudoarthrosis and do not lock against the rotation of bone fragments.

There has also been proposed (SU-A-1.463.268) an osteosynthesis clip constituted by an elastic element of U-shape, with converging legs and a curved connection element on the arc of a circle whose center is the point of convergence of the legs. The angle of the legs is comprised between 30 and 900. These legs have external teeth. The emplacement of such a clip is extremely delicate because the legs must be resiliently spaced so as to be disposed in the recesses previously formed at an angle less than the angle of the legs. The compression supplied is very uncertain and it depends on the prestress supplied by the preliminary spacing of the legs. Moreover, the connecting element is not at all adapted to the morphology of the fractured bone.

SUMMARY OF THE INVENTION

The present invention has for its object to overcome this drawback by supplying a clip which has excellent compression of the site of the fracture or of the osteotomy, and which is adapted for the treatment of numerous types of fractures, of pseudoarthroses or of osteotomy, and particularly for the treatment of fractures or pseudoarthroses of the carpal scaphoid.

To this end, the present invention has for its object an osteosynthesis clip constituted by a core and two lateral legs, the core comprising two portions inclined toward each other and forming an outwardly opening obtuse angle, the two legs terminating at their distal end in a bevel delimited by an inwardly oriented surface, and comprising a non-return device comprising teeth, characterized in that the legs are convergent and form between them an angle less than 20° and the teeth of said non-return device are formed on the external surface of said legs.

During the impaction of the clip, the legs which are slightly convergent have a tendency to spread, but the effect of the metal memory tends to bring them together, which ensures an excellent compressive effect. The non-return effect of the outwardly oriented teeth ensures the maintenance of the clip in compression with the bone fragments in a manner markedly superior to that which would be obtained by projections inwardly directed as in the mentioned U.S. Pat. No. 4,848,328 constituting the state of the closest prior art, because the quality of the bone increases with spacing from the path of the fracture or the osteotomy.

In a preferred embodiment, the cross section of the clip is circular. In this way, in all the orientations of emplacement of the clip relative to a bone, the maximum contact of the core with the bone surfaces ensured.

In a particularly preferred embodiment, internal claws are provided in the angle formed between the core of the clip in each of the lateral legs, so as to prevent the rotation of the bone fragments to be stabilized.

The clip according to the invention can be constituted by different suitable natural or synthetic materials, having mechanical properties corresponding to the given surgical use. There can be used for example a low carbon steel melted under vacuum, for example a 316 LVM alloy, or a titanium steel.

According to a preferred embodiment of the invention, the clip is a biodegradable material. The clip according to the invention is useful for maintaining in compression two bone fragments, of a fracture, of pseudoarthrosis or of osteotomy. It can be used for example for the carpal scaphoid, the joints of the toes, the joints of the fingers, the carpal bones, the bones of the tarses and of the foot.

For each of the possible applications of the clip of the present invention, it is adapted simply by selecting the appropriate angles and the dimensions such that the core of the clip will adapt to the anatomical profile of the bone in question.

The emplacement of a clip according to the present invention is effected by means of simple ancillary apparatus which, according to the invention, comprises a spacer, a series of aimers adapted to the size of the available clips, boring bits coacting with the aimer for the implantation points, a gripping impactor of the clip and a final impactor.

One of the uses of the clip of the present invention is the treatment of fractures or pseudoarthroses of the carpal scaphoid. For such a use, it is particularly desirable to choose, for the outwardly opening angle formed by the two portions of the core, an angle of 150°. Moreover, the angles formed between each of the lateral legs and the core are respectively 88° and 58°. The dimensions of the different clips are adapted to the size of the subject to be treated. In the case of the carpal scaphoid, an implantation site of the clip is located against the inter osseous ligamentary plane of the scapho-large bone and scapho-lunar, the implantation taking place with an angulation of 30° in the frontal plane to permit locating the branches of the clip in the scaphoidal body in the zone in which the grip will give the maximum solidity without passing through the adjacent intercarpal and radiocarpal articulated surfaces.

BRIEF DESCRIPTION OF THE DRAWINGS

The present invention is illustrated in greater detail with reference to the accompanying drawings showing a particular embodiment, given by way of non-limiting example.

FIG. 5 is a cross sectional view of a aimer.

FIG. 6 is an end view of the aimer of FIG. 5.

FIG. 7 is a cross sectional view of a gripping impactor of the clip.

DETAILED DESCRIPTION OF THE INVENTION

Figure 1:
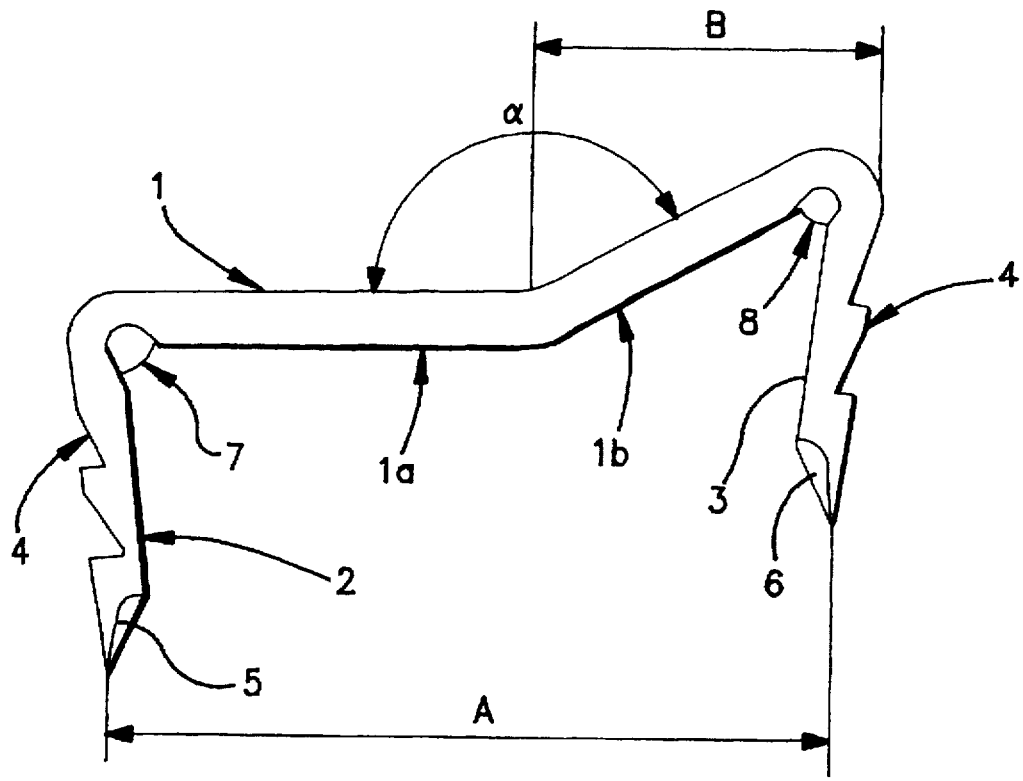
FIG. 1 is an elevational view of a clip according to the present invention.
Figure 2:
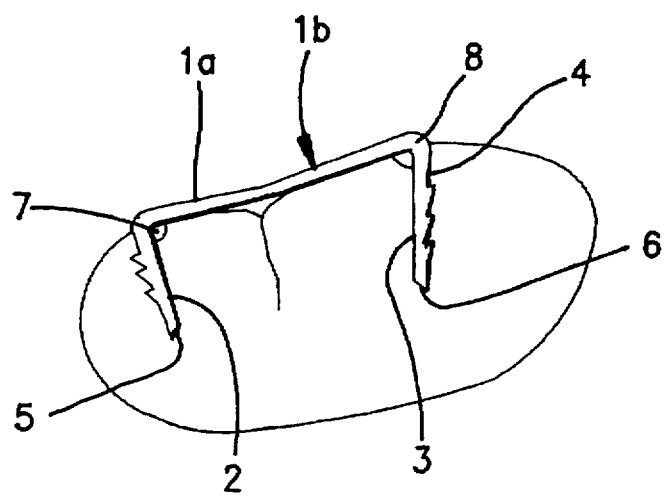
FIG. 2 is a view of a clip according to the invention, inserted in the carpal scaphoid.

The clip shown in FIG. 1 is constituted by a core 1 comprising two portions 1a and 1b, and by two legs 2 and 3. The two portions 1a and 1b of the core forming an obtuse outwardly opening angle α. Each of the legs 2 and 3 forms, with the core 1, an acute angle such that the two legs will be slightly convergent, the angle between the legs being less than 20°.

In the particular case in which the clip is adapted to be used for the carpal scaphoid, the angle α is preferably 150°, the angle formed between the leg 2 and the portion 1a is preferably 88°, and the angle formed between the leg 3 and the portion 1b is preferably 58°. This particular arrangement permits an optimum adaptation of the core of the clip against the bone and imparts to the legs their slightly convergent characteristic.

Each leg comprises, on its external surface, teeth 4. Each leg can comprise, for example, two to four teeth, preferably four. The teeth 4 can be shaped as in the illustrated embodiment, by machining the legs. However, preferably, the legs are formed projecting relative to the rest of the leg, for example by cold forming or any other appropriate technique.

The legs 2 and 3 have respectively at their distal end, a bevel 5, 6 whose surface is inwardly directed.

The core and the legs have a circular cross section. Thus, no matter what the orientation of the clip relative to the bone, the contact between the core and bone will be optimum, whilst if the core has a rectangular or a square cross section, the contact with be more or less great according to the orientation.

A claw 7 is provided in the angle formed by the leg 2 and the portion 1a of the core, and a claw 8 in the angle formed between the leg 3 and the portion 1b of the core. These claws accordingly prevent rotation of one of the bone fragments relative to the other.

A clip according to the invention having characteristics shown in FIG. 1 is perfectly adapted to be used on the carpal scaphoid. The dimensions of the legs will be adapted to the size of the subject to be treated. For example, the length of the legs 2 and 3 can be 8 mm or 10 mm, constant or variable according to the sizes of the clips, the spacing A between the distal ends of the legs can be comprised between 12 and 18 mm, the length B of the orthogonal projection of the portion 1b in the plane including the portion 1a can be between 8 and 9 mm. The diameter of the circular cross section of the core and of the legs is 1 to 1.20 mm. A range of seven different sizes within these limits permits covering substantially all the needs. The particular choice of the angles and dimensions of the clip permits a very precise adaptation of the clip to the shape of the bone, which renders ablation of the clip unnecessary when the bone is consolidated. Moreover, this clip has no tendency to limit the movement of the ankle, because it provides no abutment at the radiocarpal intra articular site.

Figure 3:
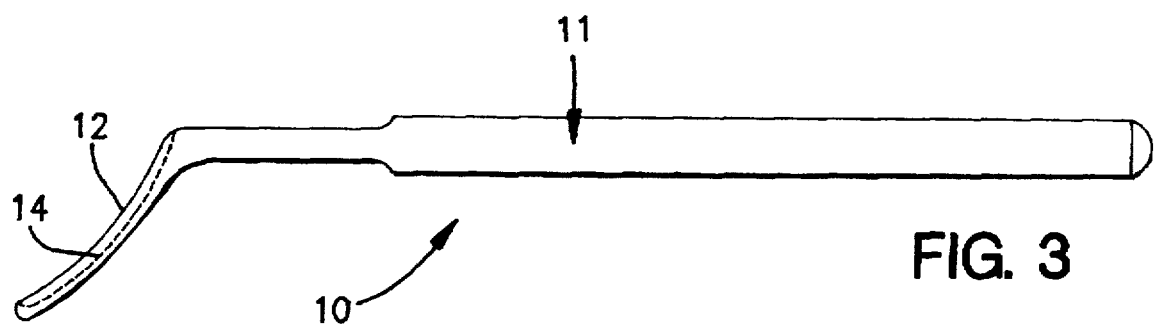
FIG. 3 is a side elevational view of a spacer.
Figure 4:
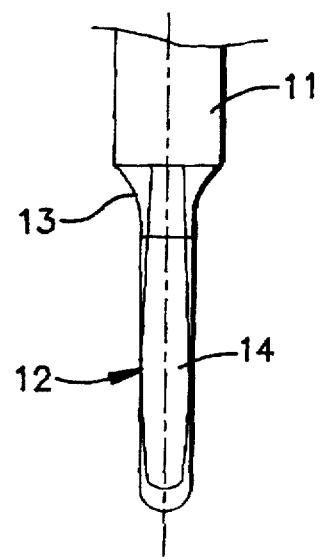
FIG. 4 is a plan view of an end of the spacer of FIG. 3.

The invention also relates to the ancillary apparatus for emplacing the clip. This ancillary apparatus comprises a spacer 10 (FIGS. 3 and 4) adapted, in the case of a carpal scaphoid fracture, to be introduced between the scaphoid and the radius so as to produce a drawing together of the two bone segments. The spacer 10 comprises a sleeve 11 terminating in a concave spoon 12 connected by a taper 13. The spoon 12 comprises a longitudinal throat 14.

The surgeon then selects, as a function of the dimensions of the bone, an aimer 20 (FIGS. 5 and 6). The aimer comprises a sleeve 21 terminating in an end 22 inclined relative to the sleeve 21 at an angle equal to the angle α of the clip 1. The aimer 20 comprises, on opposite sides of the terminal bend, two upper annular projections 23 and 24 whose bores 25 and 26 respectively open into a lower semi-circular hollow 27. The inclination and spacing of the bores 25 and 26 correspond, in combination with the shape of the lower surface of the viewer, to the dimensions of the clip to be implanted. The lower surface of viewer moreover comprises teeth 28 preventing slipping on the bone.

The surgeon, after emplacing the aimer, pierces a first securement hole by means of a broach introduced through the bore 25. He then uses a second broach to pierce a second securement hole. He then removes the broaches. The bone is ready to receive the clip.

Figure 8:
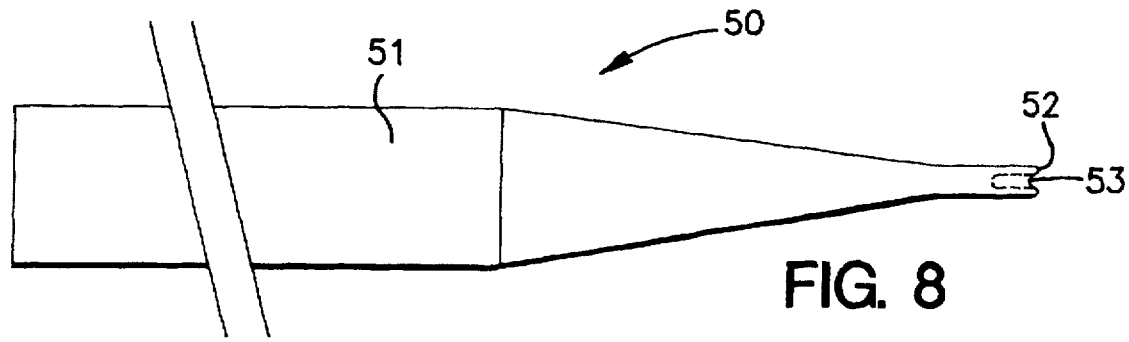
FIG. 8 is a side elevational view of a final impactor.
Figure 9:
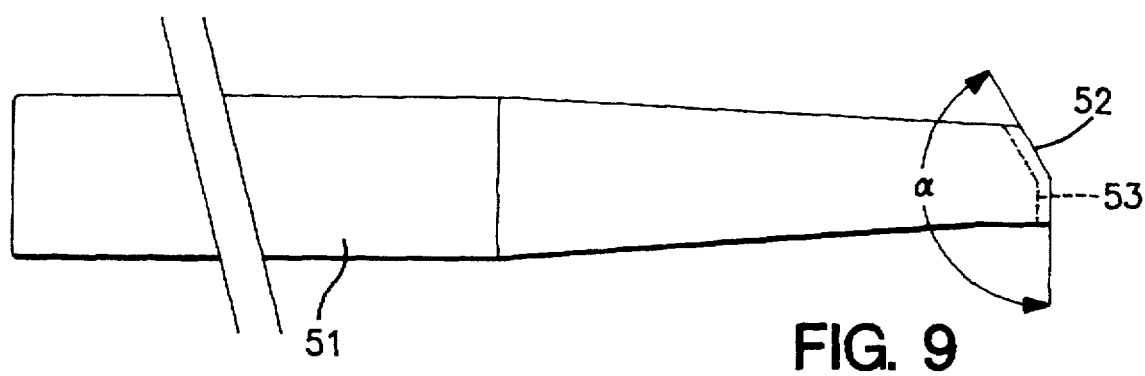
FIG. 9 is a side elevational view of the impactor of FIG. 8, turned 90° from the FIG. 8 position.

The clip is then emplaced on a gripping impactor 30 shown in FIG. 7. This latter is constituted by a support 31 sliding in a tube 32. The support 31 comprises an internally screw threaded tail 33 screwed on the external threading of the tube 32 and a head 34 provided with an axially cylindrical hollow 35 comprising an internal peripheral throat 36. A clip holder adapted to the selected clip is constituted by two half-shells 37, 38 and is mounted in the hollow 35 by a peripheral flange 39. The two half-shells 37, 38 are truncated conical apart from the flange 39 and are disposed in an internal truncated conical end 40 of the tube 32 from which they project externally. The gripping and ungripping take place by screwing and unscrewing the tail 33. The projecting end carries a clip recess 41. An internally screw threaded ring 42 for demounting is mounted on the tube 32. The gripping impactor 30 permits the precise emplacement and sinking of the clip. Complete sinking is assured by means of a final impactor 50 shown in FIGS. 8 and 9. This latter comprises a milled sleeve 51 and a head 52 provided with a throat 53 and profiled to the shape of the clip.

I claim:

1. Osteosynthesis clip comprising a core and two lateral legs, the core having two portions inclined relative to each other and forming an outwardly opening obtuse angle ($\alpha$), the two legs terminating at their distal end in a bevel delimited by an inwardly oriented surface and having an anti-return device comprising teeth, wherein the legs are convergent and form between them an angle less than 20°, and the teeth of said anti-return device are formed on an external surface of each of the legs.

2. Clip according to claim 1, wherein the transverse cross section of the core and of the legs of the clip is circular.

3. Clip according to claim 1, further comprising an internal claw in the angle formed between the core of the clip and each of the lateral legs.

4. Clip according to claim 1, wherein the clip is made of a vacuum melted low carbon steel.

5. Clip according to claim 1, wherein the clip is made of titanium steel.

6. Clip according to claim 1, wherein the clip is made of a biodegradable material.

7. Clip according to claim 1, wherein the outwardly opening obtuse angle formed by the two portions of the core is an angle of 150°, and the angles formed between each of the lateral legs and the core are respectively 88° and 58°.

8. Clip according to claim 1, wherein the length of the legs is a function of the size of the clip.

9. Clip according to claim 1, wherein the length of the legs is constant for all sizes of clip.

10. Ancillary apparatus for implanting clips of different sizes according to claim 1, comprising:

- a spacer having a sleeve including a concave spoon connected by a taper, said spoon having a longitudinal throat,
- a plurality of aimers adapted for different sizes of clips and comprising bores for guiding broaches whose inclination and spacing correspond, in combination with the shape of a lower surface of the aimer, to the dimensions of the clip to be emplaced,
- a gripping impactor arranged to receive a plurality of clip holders, corresponding to the different sizes of clips, each clip holder being mounted removably on a support sliding in a tube, a projecting end of the clip holder including a recess for the clip, and
- a final impactor provided with a head profiled to the shape of the clips and including a throat.

* * * * *